US009354148B2

(12) United States Patent
Rida (10) Patent No.: US 9,354,148 B2
(45) Date of Patent: May 31, 2016

(54) MAGNETIC PARTICLES BASED SEPARATION AND ASSAYING METHOD (71) Applicant: Spinomix S.A., Lausanne (CH)

(72) Inventor: Amar Rida, Chavannes-Renens (CH)

(73) Assignee: Spinomix, S.A., Lausanne (CH)

( * ) Notice: Subject to any disclaimer, the term of this patent is extended or adjusted under 35 U.S.C. 154(b) by 0 days.

(21) Appl. No.: 14/848,204

(22) Filed: Sep. 8, 2015

(65) Prior Publication Data

US 2016/0018303 A1  Jan. 21, 2016

Related U.S. Application Data (63) Continuation of application No. 14/190,768, filed on Feb. 26, 2014, now Pat. No. 9,157,841.

(30) Foreign Application Priority Data

Mar. 1, 2013  (CH) .......................... 530/13

(51) Int. Cl.
*G01N 33/553* (2006.01)
*G01N 1/34* (2006.01)
*G01N 33/543* (2006.01)

(52) U.S. Cl.
CPC ............ *G01N 1/34* (2013.01); *G01N 33/54326* (2013.01); *G01N 33/54333* (2013.01)

(58) Field of Classification Search
None
See application file for complete search history.

(56) References Cited

U.S. PATENT DOCUMENTS

| 3,958,068 | A | 5/1976 | Umeki et al. |
|---|---|---|---|
| 5,108,933 | A | 4/1992 | Liberti et al. |
| 5,607,768 | A | 3/1997 | Lee |
| 5,648,124 | A | 7/1997 | Sutor |
| 5,932,097 | A | 8/1999 | Wilson |
| 5,945,525 | A | 8/1999 | Uematsu et al. |
| 6,027,945 | A | 2/2000 | Smith et al. |
| 6,045,925 | A | 4/2000 | Klabunde et al. |
| 6,514,481 | B1 | 2/2003 | Prasad et al. |
| 6,773,812 | B2 | 8/2004 | Chandler et al. |
| 7,132,275 | B2 | 11/2006 | Reich et al. |
| 7,147,916 | B2 | 12/2006 | Iwasaki et al. |
| 7,232,691 | B2 | 6/2007 | Kraus et al. |
| 7,282,540 | B2 | 10/2007 | Ozaki et al. |
| 7,741,120 | B2 | 6/2010 | Klimov et al. |
| 8,142,892 | B2 | 3/2012 | Rida |
| 8,585,279 | B2 | 11/2013 | Rida |
| 2002/0187504 | A1 | 12/2002 | Reich et al. |
| 2004/0216810 | A1 | 11/2004 | Iwasaki et al. |
| 2006/0188876 | A1 | 8/2006 | Kilaas et al. |
| 2010/0157724 | A1 | 6/2010 | Rida |
| 2010/0160483 | A1 | 6/2010 | Vogt et al. |
| 2012/0329124 | A1 | 12/2012 | Tajima |

FOREIGN PATENT DOCUMENTS

| WO | WO 90/15666 A1 | 12/1990 |
|---|---|---|
| WO | WO 03/004151 | 1/2003 |
| WO | WO 2004/077044 A1 | 9/2004 |

OTHER PUBLICATIONS

Skumryev Vassil et al., Beating the superparamagnetic limit with exchange bias, Nature 423 (6942):850-53 (2003).

*Primary Examiner* — Chris L Chin
(74) *Attorney, Agent, or Firm* — Cooley LLP; Ivor R. Elrifi; Christina K. Stock (57) ABSTRACT

A magnetic particle based separation and assaying method uses at least two sets of magnetic particles placed in solution within a container and characterized respectively by a coercive field $e_1$ and $e_2$, wherein $e_1$ is greater than $e_2$. The first magnetic particles with a larger coercive field $e_1$ will be used as carrier to handle the second affinity magnetic particles having a lower coercive field $e_2$. A magnetic particles handling method includes the step of applying an external magnetic field having a polarity and amplitude that varies with time to cause the said carrier magnetic particles to be in relative motion within the container driving thereby the affinity particles to form an homogenous suspension of particles in perpetual relative movement with the respect to the liquid.

22 Claims, 3 Drawing Sheets

MAGNETIC PARTICLES BASED SEPARATION AND ASSAYING METHOD

RELATED APPLICATIONS

This application is a continuation of U.S. patent application Ser. No. 14/190,768, filed Feb. 26, 2014, which claims priority to Swiss Patent Application No. 00530/13, filed Mar. 1, 2013, each of which is herein incorporated by reference in its entirety.

FIELD OF THE INVENTION

The invention generally relates to a magnetic particles based separation and assaying method comprising a composition of magnetic particles characterized by specific magnetic responses when a fluid suspension of the said particles is subjected to an external magnetic field. Further, the invention relates to the use of magnetic particles with defined composition for assaying, manipulation and purification of biomolecules and chemical substances.

DESCRIPTION OF RELATED ARTS

In bioassays the ability to extract, concentrate and purify target molecule(s), particle(s) or analyte(s) from diverse samples (i.e. sample preparation) represents a critical step and is challenging as a prerequisite step for effective target detection and analysis. For that, magnetic responsive particles are, nowadays, considered as a standard for performing sample preparation procedures. For instance, the magnetic particles surface can be activated to carry a probe that specifically interacts with complementary target molecules. The advantage of using magnetic particles is that they can be simply manipulated using a magnetic field to control the reaction on their surface and/or to separate the specific target molecule from the initial "contaminant" surrounding medium. Magnetic particle based procedures and systems are relatively rapid, easy and require simple equipment.

One major issue that needs to be addressed in magnetic particles based assay is the homogenous dispersion of the particles during the assay processing steps. Such homogeneity is indeed crucial to maximize the total available particle surfaces in contact with the surrounding liquid medium. Moreover, the second important requirement in particles-based assay is an efficient mixing to enhance the reaction rate between the target substances and the particle surfaces. Indeed, as for any surface-based assay the reaction is strongly limited by the natural diffusion process, a strong steering and mixing is therefore necessary to promote the affinity binding reaction between the ligand and the target substance.

To address the homogeneity issue, the state-of-art magnetic particles based assay rely mostly on the use of paramagnetic or superparamagnetic particles, characterized by being capable to be magnetised in the presence of an external magnetic field but that become unmagnetized in the absence of such field. To be so, paramagnetic or superparamagnetic particles provide a magnetic response characterized by a low residual magnetisation upon the removal of the initially applied magnetic field. Such consideration is important in order to minimize the agglomeration of magnetic particles during their manipulation. Indeed, the manipulation of magnetic particles in a liquid suspension necessitates the application of a relatively "large" magnetic force, leading the monodispersed magnetic particles to agglomerate under the influence of their mutual magnetic dipole interaction. Recovering a monodispersed particles suspension after magnetic field removal necessitates, therefore, a low residual dipolar magnetization of the particles. Superparamagnetic particles as described in the prior art (as for instance in U.S. Pat. No. 6,027,945 or U.S. Pat. No. 5,945,525) suffer, however, from the limitation associated with their low magnetization under an external magnetic field, which results in difficulties in separating, dispersing and mixing such particles.

To solve the issue related to the slow separation of superparamagnetic particles, U.S. Pat. No. 5,108,933, discloses a method where monodispersed colloidal magnetic particles are "aggregated" by adding an agglomerating agent prior to their separation. In fact, by forming larger particles aggregates, the particles separation will be more efficient and faster while using a relatively lower magnetic force. However, forming such particles agglomerates can be time consuming and resuspending the particles upon their agglomeration can be difficult to achieve.

To overcome the limitations of super-paramagnetic particles, magnetic particles providing "ferromagnetic" behavior are proposed in the art. The "ferromagnetic" particle provides a magnetic response characterized by a residual magnetisation in the absence of an applied external magnetic field. With that, ferromagnetic particles present a high magnetic moment when compared with superparamagnetic particles, which makes them easier to handle using an external magnetic field.

For instance, U.S. Pat. No. 7,132,275 discloses magnetic nanowires which are elongated magnetic entities that will develop, due to their shape anisotropy, a preferential magnetization in the elongation direction of the particle. This anisotropic magnetization will remain even after the removal of the external magnetic field. In U.S. Pat. No. 8,142,892, ferromagnetic particles with tailored magnetic response are disclosed. One of the advantages of such ferromagnetic particle is the possibility to adjust their magnetic response by adjusting the "residual magnetization".

Contrary to superparamagnetic particles, ferromagnetic particles suffer, however, from a major limitation. In fact, as these particles remain magnetized upon the removal of an externally applied magnetic field, the resuspention of the particles becomes difficult. To overcome this limitation, U.S. Pat. application 2006/0188876 proposes the use of ferromagnetic particles with surfaces that comprise functional groups which promote disaggregation of the magnetic particles in the presence of a liquid phase. For instance, magnetic particle surfaces may be functionalized with a hydrophobic material that will promote the particles resuspention of the particles in an organic liquid phase or non-polar liquid phase. In U.S. Pat. No. 8,142,892, ferromagnetic particles aggregation can be effectively controlled when such particles are manipulated using a magnetic field having a polarity (i.e. magnetic field direction) and amplitude that vary with time. Nevertheless, ferromagnetic particles suffer, however, from the limitation that such particles cannot be homogenously dispersed in the absence of a magnetic field.

Knowing these shortcomings, the development of new methods allowing fast and effective handling of superparamagnetic particles is required. In other words, finding a way to combine the easy handling and homogenous mixing of the ferromagnetic particles under a magnetic field with a good dispersion of the superparamagnetic particles in the absence of an external magnetic field will be desired in conducting magnetic particles based assays.

SUMMARY OF THE INVENTION

Accordingly, the invention provides a magnetic particle based separation and assaying method. This aim is attained by using at least two sets of magnetic particles, one having a coercive field $e_1$ and another having a coercive field $e_2$, wherein $e_1$ is greater than $e_2$.

Accordingly, the invention provides a method for manipulating magnetic particles within a container by providing a first magnetic particles carrier set having coercive field $e_1$; providing a second magnetic particles affinity set having coercive field $e_2$ lower than $e_1$ and designed for selectively binding with a target molecule; placing the said sets of carrier and affinity magnetic particles in solution within a container; and applying an external magnetic field having a polarity and amplitude that varies with time to cause the said carrier magnetic particles to be in relative motion within the container thereby driving the affinity particles to form an homogenous suspension of particles in perpetual relative movement with respect to the liquid within the container.

Accordingly, the invention discloses a kit comprising a magnetic particle composition to be used for assaying, manipulation and purification of biomolecules and chemical substances. This aim is attained with a kit containing at least two sets of magnetic particles one having a coercive field $e_1$ and another having a coercive field $e_2$ wherein $e_1$ is greater than $e_2$ and reagents for assaying, manipulating or purifying biomolecules or chemical substances.

Different embodiments are set out in the dependent claims.

The current invention discloses a method of separation of target molecules or particles from a sample using magnetic particles. The method uses a combination of at least two sets of magnetic particles having a coercive field $e_1$ and $e_2$ respectively and wherein $e_1$ is greater than $e_2$. In some embodiments, $e_1$ is at least two times greater than $e_2$. The magnetic particles can be manipulated using a magnetic field having a polarity and amplitude that varies in time. For example, the magnetic field may involve a variation of frequency ranging between 0.1 to 1000 cycles per second. In various embodiments, the method additionally includes one or both of the following steps: (a) applying a first magnetic field of a frequency $f_1$ to cause the particles of the two sets to form a homogeneous suspension of particles; and/or (b) applying a second magnetic field of frequency $f_2$ lower than $f_1$ to cause the particles of the two sets to agglomerate together and form aggregates of particles. The magnetic particles may have a coating on their surface. Likewise, at least one of the sets of magnetic particles may contain an affinity recognition molecule attached to the coating for selectively binding with a target molecule.

Accordingly, the invention provides a method of handling magnetic particles in a magnetic particles separation process, wherein a first magnetic particles set having the larger coercive field $e_1$ is used as a carrier or vehicle for mixing and (or) separating the second set of magnetic particles having a coercive field $e_2$ lower than $e_1$. In a preferred embodiment, the second set of magnetic particles having the lower coercive field $e_2$, is chemically activated or conjugated to various biochemical molecules with selective target recognition capabilities (such as proteins, nucleic acids, cells, etc.).

The invention discloses a method wherein at least two sets of magnetic particles, having a coercive field $e_1$ and $e_2$ (with $e_1$ is greater than $e_2$), are added to complex reaction mixtures (such as whole blood or fragmented cells in solution) placed within a container. An external magnetic field, having a polarity and amplitude that varies with time characterized by a frequency f superior to a threshold frequency $f_1$, is applied to cause the carrier magnetic particles (those with the highest coercive field $e_1$) to be in relative motion within the container driving thereby the affinity particles (those with the lower coercive field $e_2$) to form an homogenous suspension of particles, in perpetual relative movement with the respect to the liquid within the container. This will allow effective mixing and interaction between the affinity particles and the surrounding liquid medium. This interaction will in turn result in the effective affinity binding of the target(s) to the magnetic particle surfaces.

Accordingly and upon capturing of the targets on the magnetic particles surfaces, the invention disclose a method wherein a magnetic field, having a polarity and amplitude that varies with time characterized by a frequency $f_2$ inferior to a threshold frequency $f_1$, causes the two particles sets in use to agglomerate together. Once aggregated, the particles are easy and fast to separate resulting in the separation of the target(s)—magnetic particle complex from the surrounding liquid medium.

In a preferred embodiment, the two sets of magnetic particles used in conducting an assay according to the invention are composed from a ferromagnetic particles set and a superparamagnetic particles set. The ferromagnetic particles (characterized by definition by a non-null coercive field at room temperature) are used as a carrier for mixing and separating the superparamagnetic particles (characterized by definition by a substantially null coercive field at room temperature). According to this embodiment, the superparamagnetic particles are preferably chemically activated or conjugated to various biochemical molecules with selective target recognition capabilities.

In a preferred embodiment, the two sets of magnetic particles used in conducting an assay according to the invention comprise a ferromagnetic particle set preferably characterized by a coercive field higher than 100 Oe and a superparamagnetic particles set preferably characterized by a coercive field lower than 50 Oe. In another preferred embodiment, the two sets of particles in use according to the invention comprise a first set of magnetic particle characterized by a coercive field higher than 200 Oe and a second set of magnetic particles characterized by a coercive field lower than 25 Oe.

In a preferred embodiment, the threshold frequency $f_1$ at which the two particles will "separate" and form an homogenous mixing of particles is at the minimum equal to 10 cycles per second and preferably at a minimum equal to 50 cycles per second. For this and to cause the two set of particles to agglomerate, the time varied magnetic field, according to a preferred embodiment, has a frequency lower than 10 cycles per second and preferably lower than 2 cycles per second.

Another preferred embodiment according to the invention for conducting bio-assays comprises the use of a first set of magnetic responsive particles characterized by a coercive field $e_1$ and a second set of magnetic responsive particles characterized by a coercive field $e_2$ wherein $e_1$ is at least two times greater than $e_2$.

The invention also disclose a method for manipulating magnetic particles within a container, comprising the steps of: (a) providing a first magnetic particles carrier set having coercive field $e_1$; (b) providing a second magnetic particles affinity set having coercive field $e_2$ wherein $e_2$ is lower than $e_1$. The second set of magnetic particles are preferably designed to selectively bind with a target molecule; (c) placing the said carrier and affinity magnetic particles in solution within a container; and (d) applying an external magnetic field having a polarity and amplitude that varies with time. This applied magnetic field will cause said carrier magnetic particles to be in relative motion within the container driving thereby the affinity particles to form an homogenous suspension of particles that is in perpetual relative movement with respect to the liquid within the container.

Moreover, these methods can additional include a step of separating the first and second sets of particle from the liquid solution. In a preferred embodiment the method further comprises a magnetic separation step that consists of applying a second magnetic field to cause the said two sets of particles to agglomerate together and form aggregates of particles. This separation magnetic field can be a static magnetic field or a time varied magnetic field characterized by a variation frequency lower than the frequency used to homogenize the particles during the above-mentioned step (c). In some embodiments, the frequency of the second magnetic field is lower than 10 cycles per second, and preferably between 1 and 0.1 cycles per second.

In this method, the particles of the magnetic particles carrier set may further have a coating on their surface allowing selective binding with a target molecule.

The container used in the invention refers to any container that holds the magnetic particles in suspension within a liquid that needs to be reacted with the said magnetic particles. In a preferred embodiment the container is a standard test tube. In another embodiment, the container is a reaction chamber that is part of a fluidic or microfluidic system. In the latter case, the fluidic reaction chamber is connected to a network of fluidic channels with at least one inlet and one outlet channels that will bring a sample or reagents respectively in and out the reaction chamber.

The present invention discloses also a kit comprising at least two sets of magnetic particles having a coercive field $e_1$ and $e_2$ and wherein $e_1$ is greater than $e_2$. The first set of magnetic particles (those with a larger coercive field) serves as a driver to manipulate the second set of magnetic particles (those with the lower coercive field). The latter particles are chemically activated or conjugated to various biochemical molecules with selective target recognition capabilities.

In a preferred embodiment, the driver particles with the larger coercive field are also chemically activated or conjugated to biochemical molecules with selective target recognition capabilities. In a preferred embodiment, the recognition capabilities of the deriver particles are different from the recognition capabilities of the "affinity" particles (those having a lower coercive field). Those skilled in the art will recognize that such kits can be used in life science and chemical assays.

Regarding the final goal of the invention, the invention discloses a suspension that contains functionalized magnetic particles designed to respond with a defined magnetic coercive field to the application of an external magnetic field. The said suspension of particles comprises at least two sets of magnetic particles having a coercive field $e_1$ and $e_2$ and wherein $e_1$ is greater than $e_2$. The surfaces of the said magnetic particles are specifically functionalized with affinity recognition groups for selectively binding with target molecules. With this respect the first magnetic particle set with a larger cohesive field will be used as a driver to mix or separate the low coercive field particles. With the proposed approach one will be able to take benefit from the easy handling with homogenous mixing of ferromagnetic particles (i.e. particles with a large coercive field) under an external magnetic field and the good dispersion of superparamagnetic particles (i.e. particles with a substantially lower coercive field) in the absence of an external magnetic field. The said suspension can be a part of a kit that includes other reagents required for assaying, manipulation, purification and detecting of biomolecules and chemical substances. To accomplish these objectives the magnetic particles are manipulated using an external magnetic field having a polarity and amplitude that varies with time.

BRIEF DESCRIPTION OF THE DRAWINGS

The objects and features of the present invention are set forth with particularity in the appended claims. The present invention, both as to its organization and manner of operation, together with further objects and advantages, may best be understood by reference to the following description, taken in connection with the accompanying drawings, wherein

DETAILED DESCRIPTION OF THE INVENTION

The current invention discloses a method of separation of target molecules or particles from a sample using magnetic particles. The said method involves the use of a combination of at least two sets of magnetic particles having a coercive field $e_1$ and $e_2$ and wherein $e_1$ is greater than $e_2$ The invention discloses a method wherein at least two sets of magnetic particles, having a coercive field $e_1$ and $e_2$ (with $e_1$ greater than $e_2$), are added to complex reaction mixtures (such as whole blood or fragmented cells in solution) placed within a container. An external magnetic field, having a polarity and amplitude that varies with time characterized by a frequency f superior to a threshold frequency $f_1$, is applied to cause the carrier magnetic particles (those with coercive field $e_1$) to be in relative motion within the container driving thereby the affinity particles (those with the lower coercive field $e_2$) to form an homogenous suspension of particles. This perpetual relative movement of the affinity particles with the respect to the liquid within the container allows an effective interaction (i.e. mixing) between the particles and the surrounding liquid medium. This interaction will in turn result in the affinity binding of the target(s) to the magnetic particle surfaces.

The physical mechanism underlying the invention is based on the differences in behavior or dynamics of magnetic particles with defined magnetic response (i.e. coercive field) to a magnetic field having a polarity and amplitude that vary with time.

Figure 1:
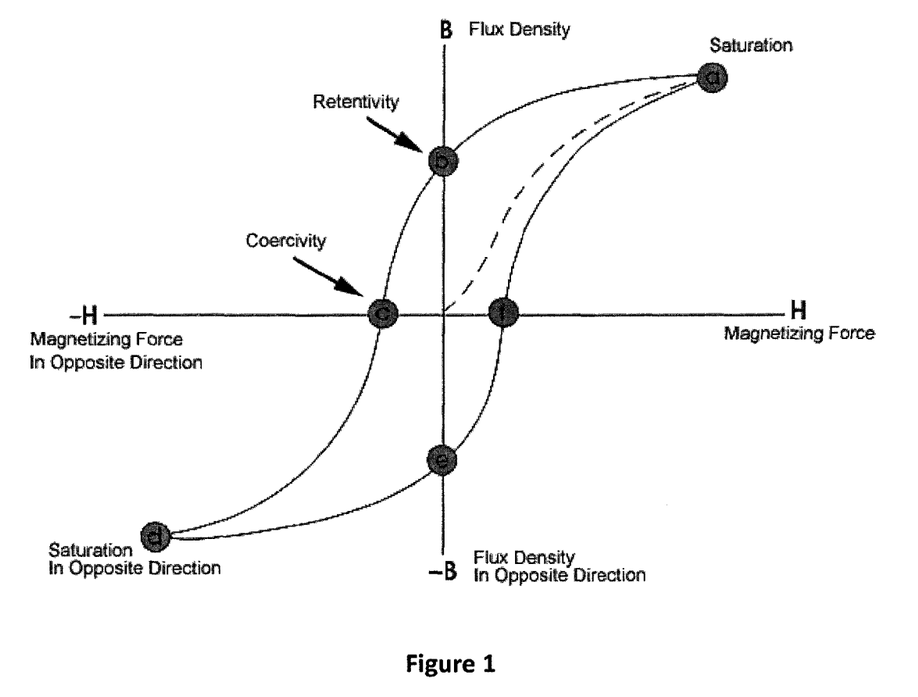
FIG. 1 is a graph showing the hysteresis response of a magnetic material (as a magnetic particle(s)) to an external magnetic field. The different key parameters of this response including the coercive field are shown.

In general, a magnetic particle (as any magnetic material) is characterized by a magnetic response defined by a magnetization "B" when subjected to an external magnetic field H. This magnetic response is represented by a B-H hysteresis curve shown in FIG. 1. A key characterization value of the B-H hysteresis curve is the coercive field or coercive force, which defines the intensity of the external applied magnetic field required to reduce the magnetization of that particle to zero after the magnetization of the sample has been driven to saturation. Practically, therefore, the coercive field (e) measures the resistance of a magnetic particle to becoming demagnetized. The coercive field is usually measured in Oersted (Oe) or ampere/meter (1 Oe=1000/4π–A/m)

With respect to their magnetic response, two types of magnetic particles are in general described in the state of art magnetic separation procedures. The first magnetic particle type, known as ferromagnetic particle, is characterized by a non-null coercive field at room temperature. In practice, we will refer herein to a ferromagnetic particle as a particle with a coercive field greater than 50 Oe and preferably a coercive field greater than 200 Oe. Ferromagnetic particles are also known by their high magnetization, which makes them easy to handle using an external low magnetic, field. However, due to the fact that they will still remain magnetized after the external magnetic particles is removed, ferromagnetic particles will tend to form aggregates of particles which make them very difficult to resuspend in the absence of an external magnetic field. However, as disclosed in U.S. Pat. No. 8,142,892, ferromagnetic particles with tailored coercive filed, show interesting behavior when manipulated using a magnetic field having a polarity and amplitude that vary in time. Under such time varied magnetic field and as disclosed in U.S. Pat. No. 8,585,279, the particles aggregation issue can be solved and the particles will present an effective homogenous mixing with the surrounding liquid medium.

The second type of magnetic particle is known as the superparamagnetic, particle, characterized by a substantially null coercive field at room temperature. In practice, we will refer herein to the superparamagnetic particle as a particle with a coercive field inferior 50 Oe and preferably a coercive field inferior 20 Oe. Due their low coercive field, superparamagnetic particles tend to lose their magnetization upon removal of the externally applied magnetic field. Under such conditions, the particles will be easily resuspended to form a homogenous suspension of particles, which makes them preferable for bioassay applications. However, an important limitation associated with superparamagnetic particle is that these magnetic particles present a low magnetization under an external magnetic field. In this case, a high magnetic field is necessary to create a sufficient magnetic force to manipulate these particles. Moreover, such particles are more difficult to handle and mix using an external magnetic field as superparamagnetic particles will tend to form aggregates even when a time varied magnetic field is used, as disclosed in U.S. Pat. No. 8,585,279.

Finding a way to combine the easy handling and homogenous mixing of ferromagnetic particles under an external (time varied) magnetic field and the good dispersion of superparamagnetic particles in the absence of an external magnetic field is therefore desired for conducting magnetic particles based assays.

Figure 2:
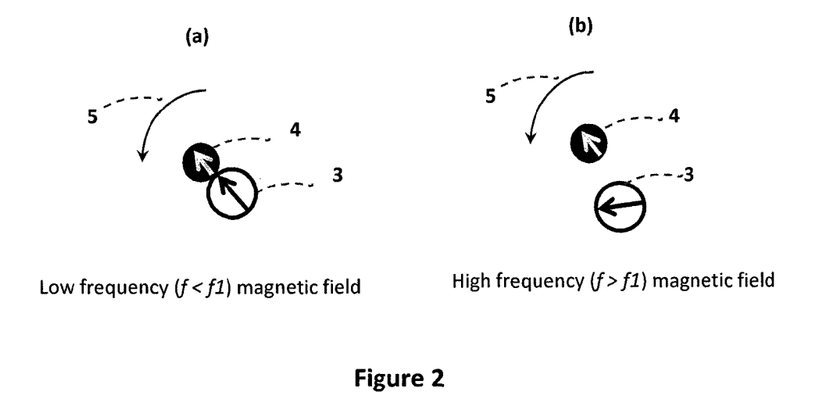
FIG. 2 is a schematic illustration of the physical mechanism underlying the magnetic particles handling method according to the invention and where a high and low coercive field particles are manipulated using an external magnetic field having a polarity and amplitude that varies in time. At a low frequency (FIG. 2 (a)) the two sets of particles will agglomerate while at a high frequency (FIG. 2 (b)) the particles will tend to be separated (repulsed) from each other.

The physical mechanism underlying the particles handling method according to the invention is shown in FIG. 2. This mechanism is essentially based on the difference in the dynamic behavior of the magnetic response of particles having different coercive field under the application of an external magnetic field having a polarity and amplitude that varies in time (i.e. time varied magnetic field).

Accordingly, the said magnetic field variation is characterized by a variation frequency ranging between 0.1 to 10000 cycles per second. In a preferred embodiment, magnetic field variation is characterized by a variation of frequency ranging between 1 to 500 cycles per second.

In such time varied magnetic field and as illustrated in FIG. 2(a), when a high coercive field $e_1$ magnetic particles (3) (represented in an empty circle) in combination with second particle, (4) having a (relatively) lower coercive field $e_2$ (represented in black circle) are manipulated using a low frequency time varied magnetic field, the two particles tend to agglomerate together. This agglomeration under a low frequency time varied magnetic field, as in the case of a static magnetic field, is due to the fact that the two particle types will "rotate" in a synchronized way with the external field polarity variation (or "rotation"). Under such condition, the two particle types (high and low coercive field) can follow the "slow" field polarity variation which leads their respective magnetic moment to be aligned and therefore the particles will have an attractive interaction between them (thus their aggregation).

At a high frequency time varied magnetic field and due to the high viscosity torque exerted by the surrounding liquid medium, the magnetic moment of the particles will tends to be desynchronized with respect to the field polarity variation (or rotation) of the external magnetic field. The high frequency regime will be therefore characterized by a time "lag" between the magnetic field variation and the magnetic moment of the particles. This time lag is lower as the coercive field of the particle is higher (i.e. particles with a high coercive field will tends to follow the magnetic field variation more easily). As illustrated in FIG. 2(b), when a high coercive field $e_1$ magnetic particle (3) (represented in an empty circles) in combination with a second particle (4) having a (relatively) lower coercive field $e_2$ (represented by a black circle) are manipulated using a high frequency time varied magnetic field, the two particles tend to be separated (i.e. desegregated) from each other due to the negative (i.e. repulsive) magnetic interaction created by the "lag" between their respective magnetic moment at a high frequency magnetic field. By further increasing the frequency of the polarity variation of the external magnetic field one can reach practically a frequency threshold ($f_1$) where only the particle (3) with the high coercive field can still be dynamically moving and follow the field while the particle (4) with the low coercive magnetic field have a relatively low physical movement.

Using this physical mechanism, the invention discloses a method for manipulating magnetic particles which involves the use of a combination of at least two sets of magnetic particles having a coercive field $e_1$ and $e_2$ with $e_1$ greater than $e_2$ and where in operation includes the steps: (a.) Applying a first magnetic field characterized by a frequency $f_1$ to cause the two particles in use to form an homogenous suspension of particles; and (b.) Applying a second magnetic field with a frequency $f_2<f_1$ to cause the particles in use to agglomerate together and form aggregates of particles.

Regarding the frequencies of the time varied magnetic field according to the invention, in a preferred embodiment the threshold frequency $f_1$ at which the two particles will "separate" from each other and form a homogenous mixing of particles is at a minimum equal to 10 cycles per second and preferably at a minimum equal to 50 cycles per second. Practically, the higher the coercive field ($e_1$) of the first particle set when compared to the coercive field ($e_2$) of the second particle set; the higher should be the threshold frequency $f_1$ necessary to separate the two particles to form a homogenous state. Given these references of the threshold frequency $f_1$, to cause the two sets of particles to agglomerate the time varied magnetic field should have a frequency lower than 10 cycles per second and preferably lower than 2 cycles per second.

The magnetic particles handling according to the invention is performed using a time varied magnetic field generated by at least one couple of magnetic poles facing each other across a gap, preferably according to U.S. Pat. No. 8,585,279 herein incorporated entirely as a reference. Accordingly, the invention discloses, the use of magnetic field sequences having polarity and amplitude that vary in time to induce time variations of the position of the magnetic field gradient maxima across a reaction chamber, causing thereby the particles in use to be in relative translational and rotational motion as a fog of particles over the whole reaction chamber volume. The first key element in the actuation mechanism according the invention is a "base" magnetic field actuation of the magnetic poles which is a magnetic field with a polarity and amplitude that vary with time. A typical example of this actuation field is an oscillating magnetic field as the one of equation: $B=B_0 \sin(f t)$. In general, such base magnetic actuation field has a substantially rectangular, sinusoidal, saw-tooth, asymmetrical triangular or symmetric triangular form or any combination of such forms. The "reaction chamber" that is part of a microfluidic network as used herein refers to chambers with a cavity that have a volume in the range of 0.1 µl to 500 µl and is used for containing the said magnetic particles in suspension and placed in the gap of the said electromagnetic poles, wherein the reaction chamber has inlet/outlet ends for introducing and removing the liquid medium into and from the reaction chamber. In a preferred embodiment, the facing poles are diverging from a narrow end of the gap to a large end of the gap and the reaction chamber is extending between its ends along said gap such that the ends of the reaction chamber are in correspondence with the narrow and large ends of the gap. The diverging/converging parts of the reaction chamber are placed in the gap of at least one couple of magnetic poles, wherein the magnetic poles are arranged co-divergently/co-convergently with the reaction chamber's converging/diverging parts. In some embodiments, the magnetic poles form a quadrupole comprising (i) a first couple of magnetic poles facing each other forming a diverging gap and (ii) a second couple of magnetic poles facing each other and forming a diverging gap, with the large ends of the diverging gaps of the first and second couples of poles facing one another, and (iii) a reaction chamber that is part of a fluidic network, having a cavity with diverging parts of the reaction chamber that are arranged co-divergently in the diverging gaps between the poles. In these methods, the key finding is to apply in each electromagnetic pole magnetic field sequences having polarity and intensity that vary in time, the role of which is to effectively break or control the particle aggregates and to maintain the particles in suspension as a fog of particles in relative dynamic motion; and then combining the magnetic fields from different magnetic poles in a sequence to induce homogeneous mixing of the particles over substantially the whole reaction chamber volume. In the invention by "field sequences having polarity and intensity that vary in time" one means the composition of the "base" actuation field on each magnetic pole along with its sequential variation to induce the particles movement across the reaction chamber volume. In practice indeed, one can decompose the field sequences actuating each magnetic pole in two main components: (1) a base actuation field component that has a polarity and amplitude that vary with time and (2) a sequential variation of this base actuation field to induce the particles displacement across the reaction chamber and thereby affecting particles mixing. The present invention concerns the magnetic poles actuation mechanism which consists of: (1) applying from the electromagnetic poles magnetic field sequences having polarity and intensity that vary in time; said varying magnetic field sequences being effective to break or inhibit particle claim aggregates and to maintain the particles in suspension as a fog of particles in relative dynamic motion; and (2) combining the magnetic fields from different magnetic poles in a sequence to induce displacement of the fog of particles across the reaction chamber whereby the fog of particles occupies substantially the whole reaction chamber volume quasi-instantaneously or over a period of time. Using this method, the particle mixing will provide a considerable and perpetual increase of the active surface of particles par unit of volume leading to an enhanced contact between this large surface of particles and the target substances. Further, the proposed magnetic particles handling process advantageously assures a homogenous mixing over the whole reaction volume in a fraction of time allowing thereby much more sample volume to be effectively and rapidly contacted with the particle surfaces. Moreover, during their manipulation the particles are in perpetual effective movement over the whole reaction chamber volume, which is a key in enhancing particles mixing. In a different embodiment, rather than having a flow-through for capturing targets from a large sample volume, a target concentration can be achieved in a more controlled way under a static (no-flow) condition. This embodiment, is based on the use of the concept of "pulsed injection" (instead of continuous flow) of the sample in the reaction chamber followed by a homogenous mixing of the particles. More specifically, in a first step the particles are attracted to the reaction chamber walls (i.e., a sub-volume of the reaction chamber at the outer borders of the reaction chamber) and retained while a defined volume of the sample, that preferably will not exceed the reaction chamber volume, is injected. In a second step, the particles coated with specific capturing probe will be mixed to homogenously cover the reaction chamber. After mixing of a defined time period, the particles will be attracted again to the reaction chamber walls and the new sample volume injected to the reaction and then mixed. This process will be repeated in sequential way until the full sample volume is mixed with the magnetic particles.

The magnetic particles used according to the invention and particularly the first set of particles having the larger coercive field are preferably composed from ferrimagnetic or ferromagnetic particles. Preferably, the first set of magnetic particles is as disclosed in U.S. Pat. No. 8,142,892 herein incorporated entirely as a reference. With this respect, the magnetic particles in use according to the invention are composed of a ferromagnetic that includes, but is not limited to, Cobalt (Co), Nickel (Ni), magnetite ($\gamma$-$Fe_2O_3$) or any alloy thereof. Some ferromagnetic alloys having a high magnetization and strong axial magnetocrystalline anisotropy, such as, Pt, FePt, $PrCo_5$, Sm and CoPt, are preferably used to provide a high coercive field. In general transition metals, metals oxides and their alloys are preferred materials entering in the composition.

The magnetic particles used according to the invention and particularly the second set of particles having the lower coercive field are preferably composed of paramagnetic or superparamagnetic materials. As described in the art, the material entering in the composition of superparamagnetic particles is fine (little nanometer size) magnetic particles (known also as Ferro-fluid suspensions). In fact, when using finer magnetic particles as primary magnetic material, the direction of the residual magnetization of the fine particles is so small that it can be reversed by the surrounding thermal energy fluctuations, leading to a vanishing average residual magnetization.

According to an embodiment of the invention, the magnetic particles have a coating on their surface and wherein at least one set of the said magnetic particles comprises an affinity recognition molecule attached to their coating for selectively binding with a target molecule. For this, the magnetic particle surface comprises for example a functional group or a ligand that is capable of binding to a target molecule or to class of target molecules. Potential functional groups comprise but are not limited to carboxylic acids, hydroxamic acids, non-adhesive compounds, amines, isocyanates, and cyanides. Potential ligands comprise but are not limited to proteins, DNA, RNA, enzymes, hydrophobic materials, hydrophilic material, and antibodies. More generally, examples of ligands suitable for use in the present invention include, but are not limited to, molecules and macromolecules such as proteins and fragments of proteins, peptides and polypeptides, antibodies, receptors, aptamers, enzymes, substrates, substrate analogs, ribozymes, structural proteins, nucleic acids such as DNA and RNA and DNA/RNA hybrids, saccharides, lipids, various hydrophobic or hydrophilic substances, lipophilic materials, chemoattractants, enzymes, hormones, fibronectin and the like. Such molecules and macromolecules may be naturally occurring or synthetic. The term ligand may also include larger entities such as cells, tissues, entire microorganisms, viruses, etc.

Figure 3:
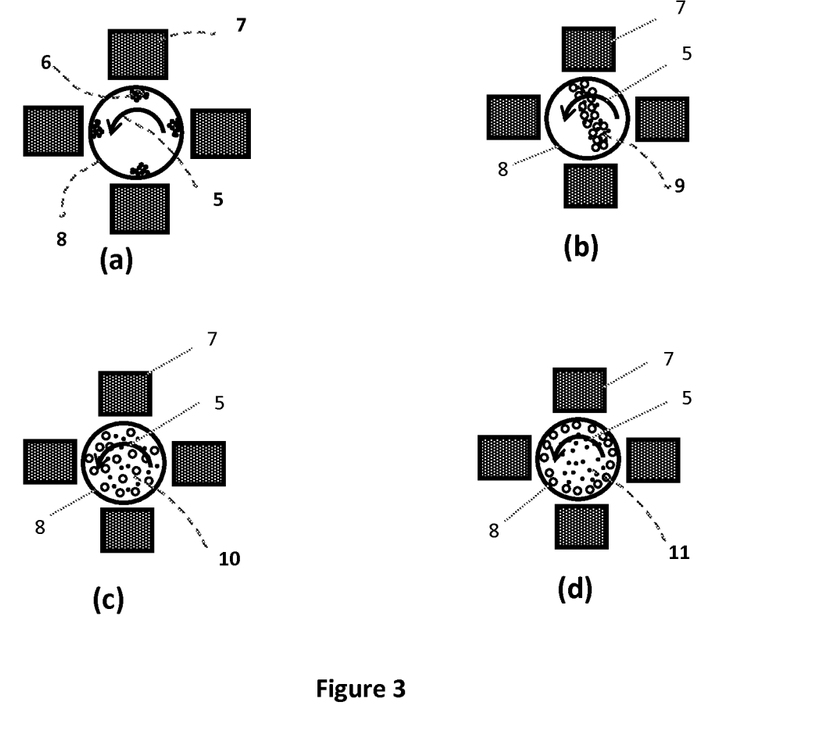
FIG. 3 is a schematic illustration of magnetic particles handling method according to the invention. Particularly, the illustration shows the behavior of magnetic particles in suspension within a container subjected to a magnetic field having a polarity and amplitude that varies in time generated by a serial actuation of magnetic sources surrounding the container.

FIG. 3 (a) shows the behavior of low coercive field particles (6) manipulated in a container (8), as for instance superparamagnetic particles in a high frequency varied magnetic field. Under such conditions, the particles will tend to agglomerate at the outer borders of the container close to the magnetic field sources (7) surrounding the container (8) and which cause serial actuation of a magnetic field. FIG. 3 (b) shows the behavior of a combination (9) of a high coercive (empty circle) particles and low coercive particles (dark circle) in a low frequency time varied magnetic field (5). Under such conditions, the high coercive field particles will drive the low coercive field particles in the form of aggregates of particles (9) moving with the polarity variation of the external magnetic field (5). FIG. 3 (c) shows the behavior of a combination (10) of a high coercive (empty circle) particles and low coercive particles (dark circle) in a high frequency time varied magnetic field (5). Under such conditions, the high coercive field particles will drive the low coercive field particles in the form of a homogenous suspension of particles (10) moving with the polarity variation of the external magnetic field (5). FIG. 3 (d) shows the behavior of the particles as for FIG. 3 (c) but with higher amplitude of the external magnetic field. Under such conditions and due to their higher magnetization, the high coercive field particles will be attracted to the outer border of the container while the low coercive field particles still form a homogenous suspension of particles (11) moving with the polarity variation of the external magnetic field (5).

Figure 4:
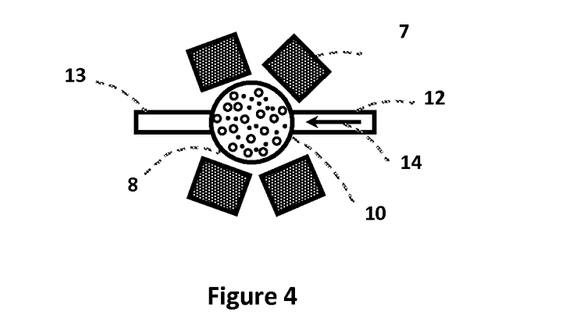
FIG. 4 is a schematic representation of the container according to an invention embodiment which comprises a reaction chamber connected to a network of fluidic channels with at least one inlet and one outlet channel that will bring, by a flow-though, a sample or reagents respectively in and out of the reaction chamber.

FIG. 4 is a schematic representation of a container according to an embodiment of the invention which comprises a reaction chamber (8) connected to a network of fluidic channels by at least one inlet (12) and at least one outlet (13) that will deliver, by a flow-though (14), a sample or reagents respectively into and out of the reaction chamber (8). As before, magnets (7) are disposed around the chamber (8) for application of a time varied magnetic field.

The container used in the invention refers to any container that holds the magnetic particles in suspension within a liquid that needs to be reacted with the said magnetic particles. In a preferred embodiment the container is a standard test tube. In another embodiment, the container is a reaction chamber that is part of a fluidic or microfluidic system. In the latter case, the fluidic reaction chamber is connected to a network of fluidic channel with at least one inlet and one outlet channel that will bring a sample or reagents respectively into and out of the reaction chamber. This container will be placed within a device that will subject the said reaction chamber to a magnetic field and more particularly to a time varied magnetic field as described above.

Another aspect of the invention concerns a suspension that contains at least two types of magnetic particles with a defined magnetic coercive field responsive to an external magnetic field. The surfaces of the said magnetic particles are specifically functionalized with affinity recognition groups for selectively binding with target molecules. The said suspension is a part of a kit that includes other reagents required for assaying, manipulation and purification of biomolecules and chemical substances. In a preferred embodiment, the kit according to the invention comprises at least one set of magnetic particles characterized by superparamagnetic behavior at room temperature and at least one set of magnetic particles characterized by a ferromagnetic behavior. The ferromagnetic particles have preferably a coercive field ranging from 100 to 1000 Oe. In operating the magnetic particles according to the invention magnetic field sequences having polarity and amplitude that vary in time are manipulated to cause homogenous mixing over the whole reaction volume.

While the present invention has been described through particular illustrative embodiments, it is not to be restricted by those embodiments but only by the appended claims. Accordingly, the invention will include any changes, modifications or combinations of the embodiments without departing from the scope of the invention.

The invention claimed is:

1. A method of mixing magnetic particles with a reagent in a reaction chamber that is part of a microfluidic network and that contains the magnetic particles in suspension, wherein the magnetic particles comprise at least two sets of magnetic particles, wherein one set are carrier magnetic particles having a coercive field $e_1$ and wherein one set are affinity magnetic particles having a coercive field $e_2$ wherein $e_1$ is greater than $e_2$, the method comprising the steps of:
   a. providing at least two magnets that generate or can be configured to generate a magnetic field having polarity and intensity that vary in time within the reaction chamber; and
   b. applying a first magnetic field having a polarity and intensity that varies in time with a frequency $f_1$ to cause the particles of the two sets to form a homogeneous suspension of particles.

2. The method according to claim 1, wherein $e_1$ is at least two times greater than $e_2$.

3. The method according to claim 1, wherein the magnetic particles have a coating on their surface and wherein at least one set of said magnetic particles comprises an affinity recognition molecule attached to their coating for selectively binding with a target molecule.

4. The method according to claim 1, wherein the particles of the carrier particle set are ferromagnetic.

5. The method according to claim 1, wherein the particles of the affinity particle set are paramagnetic.

6. The method according to claim 1, wherein the frequency of said first magnetic field is greater than 10 cycles per second.

7. The method according to claim 6, wherein the frequency of said magnetic field is greater than 100 cycles per second.

8. The method according to claim 1, wherein the method comprises a separation step that comprises applying a second magnetic field to cause said first and second sets of particles to agglomerate together and form aggregates of particles.

9. The method according to claim 8, wherein said second magnetic field is a static magnetic field.

10. The method according to claim 8, wherein said second magnetic field has a polarity and intensity that varies with time with a frequency $f_2$ lower than $f_1$.

11. The method according to claim 10, wherein the frequency of said second magnetic field is lower than 10 cycles per second.

12. The method according to claim 1, wherein the magnetic particles carrier set further have a coating on their surface allowing selective binding with a target molecule.

13. The method according to claim 1, wherein the frequency of said second magnetic field is between 2 and 0.1 cycles per second.

14. The method according to claim 1, wherein the particles of the carrier particle set have a coercive field higher than 100 Oe.

15. The method according to claim 1, wherein the particles of the affinity particle set have a coercive field lower than 50 Oe.

16. The method according to claim 1, wherein the reaction chamber comprises a narrow end and a large end that are connected to inlet and outlet ends for introducing and removing the liquid medium into and from the reaction chamber, and wherein the magnets comprises at least two electromagnetic poles face each other across the reaction chamber.

17. The method of mixing particles according to claim 1, wherein the reaction chamber comprises a cavity with at least one segment with diverging/converging parts, and at least one couple of electromagnetic poles face each other across the reaction chamber and geometrically arranged in a way to be co-diverging/co-converging with diverging/converging parts of the reaction chamber.

18. The method according to claim 1, wherein the magnetic poles form a quadrupole configuration.

19. The method according to claim 1, wherein the volume of the reaction chamber is between 0.1 µl to 500 µl.

20. The method according to claim 1, wherein the time varied magnetic field of the step b comprises:
   c. applying from the magnets a magnetic field having polarity and intensity that vary in time with a frequency f1, being effective to break and inhibit the two sets particles from forming aggregates and to maintain the particles in suspension as a fog of particles in relative dynamic movement;
   d. combining the magnetic fields from the magnets in a sequence to induce displacement of the fog of particles across the reaction chamber whereby the fog of particles form an homogeneous suspension of particles within the reaction chamber volume.

21. The method according to claim 1, wherein the method further comprises the steps:

c. separating said first and second sets of particles from the reagent solution so the particles occupy a sub-volume in the volume of the reaction chamber;

d. injecting a defined volume of the reagent in the reaction chamber;

e. applying a magnetic field having a polarity and intensity that varies in time with a frequency f1 to cause the particles of the two sets to form a homogeneous suspension of particles within the reaction chamber volume; and f. repeating in sequential way the steps c-e until the full reagent volume is mixed with the magnetic particles.

22. The method according to claim 1, wherein the method further comprises a step of applying a time varied magnetic field having a polarity and intensity that varies in time to cause the carrier particles to be attracted to an outer border of the container of the reaction chamber while the affinity particles from a homogeneous suspension of particles.

* * * * *